United States Patent [19]

Singh et al.

[11] 4,288,553

[45] Sep. 8, 1981

[54] DISOPYRAMIDE COMPOUNDS FOR CONJUGATING PROTEINS USED IN IMMUNOASSAYS FOR DISOPYRAMIDE

[75] Inventors: Prithipal Singh, Sunnyvale; Pyare L. Khanna, San Jose; Floyd W. Colvin, Redwood City, all of Calif.

[73] Assignee: Syva Company, Palo Alto, Calif.

[21] Appl. No.: 120,590

[22] Filed: Feb. 11, 1980

[51] Int. Cl.³ .................. C12N 9/96; G01N 33/54; C02D 211/00
[52] U.S. Cl. .................................. 435/188; 435/7; 260/112 R; 260/112 B; 260/121; 424/12; 424/85; 546/333
[58] Field of Search ............... 435/188, 7; 260/122 R, 260/122 B, 121; 546/333; 424/12, 85

[56] References Cited

U.S. PATENT DOCUMENTS

| | | | |
|---|---|---|---|
| 3,225,054 | 12/1965 | Cusic | 546/333 |
| 3,852,157 | 12/1974 | Rubenstein et al. | 435/188 |
| 3,878,187 | 4/1975 | Schneider et al. | 435/7 |
| 4,026,879 | 5/1977 | Spector | 260/121 |
| 4,235,969 | 11/1980 | Singh et al. | 435/188 |

*Primary Examiner*—Lionel M. Shapiro
*Attorney, Agent, or Firm*—Bertram I. Rowland

[57] ABSTRACT

Novel carboxyalkylated disopyramides (NOR-PACE®) are provided as precursors for conjugating proteins, either antigenic for the preparation of antibodies or enzymatic for the preparation of enzyme conjugates, which antibodies and enzyme conjugates find use as reagents in immunoassays. The combination of antibodies and enzyme conjugates provide for sensitive, accurate, rapid assays for disopyramide without interference from closely analogous compounds, such as methadone or disopyramides metabolites.

12 Claims, No Drawings

DISOPYRAMIDE COMPOUNDS FOR CONJUGATING PROTEINS USED IN IMMUNOASSAYS FOR DISOPYRAMIDE

BACKGROUND OF THE INVENTION

1. Field of the Invention

Because of the many side effects, particularly toxic effects, of drugs used for treatment of a wide variety of medical disorders, it is necessary to monitor the blood level of the drug, to insure that a therapeutic dosage is maintained, while preventing toxic dosages. In the treatment of arrhythmia, disopyramide is employed. The therapeutic range is believed to be between about 2 to 4 μg/ml, but this may vary with the patient. At greater than 7 μg/ml, the patient runs a high risk of toxic effects, particularly anticholinergic effects. It is therefore necessary that the amount of drug in the blood stream be monitored within the narrow level of therapeutic activity, while assuring that the level is below the toxic level.

2. Description of the Prior Art

A large number of haptens have been described as antigen conjugates and enzyme conjugates. See for example U.S. Pat. Nos. 3,817,837, 3,878,187 and 4,026,879. Disopyramide is a commercially available compound sold by G. D. Searle.

SUMMARY OF THE INVENTION

N-Carboxyalkylene derivatives of disopyramide are provided as precursors for conjugating proteins, such as antigens and enzymes. The antigens are used for production of antisera to disopyramide, which antisera together with the enzyme conjugates are used as reagents in sensitive immunoassays for monitoring disopyramide in serum.

DESCRIPTION OF THE SPECIFIC EMBODIMENTS

N-Carboxyalkylene disopyramides are provided as precursors to protein conjugates, where the proteins are antigens or enzymes. The antigenic conjugates are employed for the production of antibodies which are used in conjunction with the enzyme conjugates in sensitive immunoassays for disopyramide.

For the most part, the compounds of the subject invention will have the following formula:

$$(A-CONHR(CO)_m)_n Z$$

wherein:
A will be of the formula:

A = 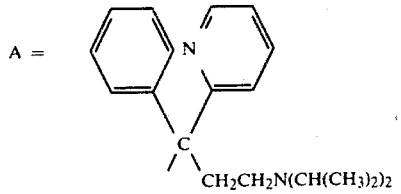

R is a linking group of at least one carbon atom and not more than about six carbon atoms, usually one to three carbon atoms, which are saturated aliphatic, preferably polymethylene;

Z is hydrogen, oxy including hydroxyl, alkoxyl of from one to six, usually from one to three carbon atoms, or an activated ester capable of amide formation in an aqueous medium, e.g. N-oxysuccinimide and p-nitrophenoxy, or a poly(amino acid), including polypeptides and proteins, which is antigenic or an enzyme, which poly(amino acid) is joined by a bond to a methylene group when m is zero and by an amide bond when m is one;

m is zero or one when Z is a poly(amino acid) and is otherwise one; and n is one when Z is other than a poly(amino acid) and is otherwise one to the molecular weight of Z divided by 500, more usually divided by 1,000 and frequently divided by 1500, generally ranging from one to 500, preferably from 10 to 100, when Z is an antigen and from one to 30, more usually two to 20, and preferably from two to 16, when Z is an enzyme.

Illustrative R groups include methylene, ethylene, propylene, and 1-methylethylene.

For those compounds where n is one, the compounds will be of the following formula:

$$ACONHR^1 COZ^1$$

wherein:
all of the symbols have been defined previously except for $R^1$, which comes within the definition of R, and is preferably alkylene of from one to two carbon atoms; and $Z^1$ is hydrogen, or oxy (as defined for Z).

Where Z is a poly(amino acid), the compounds will for the most part have the following formula:

$$(ACONHR^2(CO)_{m2})_{n2} Z^2$$

where all the symbols have been defined previously except for:

$R^2$ which is the same as $R^1$;

$Z^2$ is a poly(amino acid), which is either antigenic or an enzyme;

$m^2$ is zero or one, preferably one; and $n^2$ is at least one, and usually greater than one; when $Z^2$ is antigenic, $n^2$ will normally be at least two and not greater than the molecular weight of $Z^2$ divided by 500, usually not greater than the molecular weight of $Z^2$ divided by 1,000 and preferably not greater than the molecular weight of $Z^2$ divided by 1500, generally ranging from two to 500, usually 4 to 100; when $Z^2$ is an enzyme, $n^2$ will be at least one, usually not greater than 30, more usually in the range of two to 20, and preferably in the range of about two to 16.

The poly(amino acids) will generally range from about 5,000 molecular weight, having no upper molecular weight limit, normally being less than 10,000,000 usually not more than about 600,000. There will usually be different ranges, depending on whether an antigen or an enzyme is involved, with antigens ranging from about 5,000 to $10^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100.

With lower molecular weight antigens, below 35,000, the number of conjugates will generally be in the range of from about 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the disopyramide is to be measured. Primarily, the enzymes of choice, based on the I.U.B. classification are: Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

The subject precursor can be prepared by the carboxyalkylation of the amide anion using a haloacylester, particularly a bromoacylester, more particularly an alphahaloacylester. Specifically, the parent amide may be combined with a hydride e.g. sodium hydride in a polar aprotic solvent at elevated temperatures, generally not exceeding about 100° C. After careful hydrolysis of the ester, a reactive ester, such as the N-hydroxy succinimide may be prepared for conjugation to proteins.

By employing the above procedure, disopyramide is functionalized to a compound which can be readily conjugated to poly(amino acids), either antigenic or enzymes. The structure of the disopyramide is retained during the synthetic procedure and those elements of the structure which provide for distinctions between closely similar compounds are exposed to allow for formation of antibodies which are capable of distinguishing disopyramide from similarly structured compounds, such as the hydroxylated phenyl and dealkylated metabolites.

The antigen compounds may be injected into a wide variety of vertebrates in accordance with conventional methods for the production of antibodies. Usually, the animals are bled periodically with successive bleeds having improved titer and specificity, then plateauing and diminishing in their specificity and titer. The antigens may be injected intramuscularly, intraperitoneally, subcutaneously, or the like. Usually, a vehicle is employed, such as complete or incomplete Freund's adjuvant.

As previously indicated, the antibodies and enzyme reagents prepared in accordance with the subject invention find particular use in immunoassays for the determination of disopyramide. A description of the method for carrying out a homogeneous enzyme immunoassay may be found in U.S. Pat. No. 3,817,837. The method involves combining the enzyme conjugate, the unknown sample suspected of containing disopyramide, and an antibody for disopyramide in an aqueous buffered medium at temperatures in the range of about 10° to 50° C., usually from about 20° to 40° C., and determining the enzyme activity as compared to the enzyme activity of an assay medium having a known amount of disopyramide.

The following examples are offered by way of illustration and not by way of limitation.

EXPERIMENTAL (All temperatures not otherwise indicated are in centigrade. All parts and percents are by weight, except for mixtures of liquids which are by volume. The following abbreviations are used: THF—tetrahydrofuran; DCC—dicyclohexyl carbodiimide; G6PDH—glucose-6-phosphate dehydrogenase; G6PNa$_2$—disodio glucose-6-phosphate; EDAC—ethyl 3-dimethylaminopropyl carbodiimide; NHS—N-hydroxy succinimide; DMF—dimethylformamide; BSA—bovine serum albumin; BGG—bovine gamma-globulin.).

I. Preparation of 4-Diisopropylamino-2-Phenyl-2-(2'-Pyridyl)-Butyramide.

(See U.S. Pat. No. 3,225,054 for procedure).

2-Phenyl-2-(2'-pyridyl)-4-diisopropylaminobutyronitrile (10.0 g, 0.031 moles) was heated with 125 ml conc. H$_2$SO$_4$ to 100° for one hour. After cooling with ice and adding ice to the flask, the solution was adjusted to pH8 with 10 N NaOH, when some inorganic salts precipitated out. The pH was adjusted to 5 with glacial acetic acid, then extracted once with benzene. The pH was then adjusted to >10 and the solution extracted with CH$_2$Cl$_2$ three times. The CH$_2$Cl$_2$ extracts were dried over MgSO$_4$ and solvent removed under vacuum to give a yellow gum. The gum was recrystallized in hot hexane to give 6.0 g of the amide in the first crop, 3.0 g in a second crop. TLC showed one major spot Rf=0.3. The nitrile Rf=0.8 (75-25, ether—CHCl$_3$ sat. with NH$_3$ gas.)

II. Preparation of N-Ethoxycarbonylmethyl 4-Diisopropylamino-2-Phenyl-2-(2-pyridyl) Butyramide.

The amide (5.0 g, 14.7 mmoles, prepared in Ex. I) was dissolved in 50 ml of dioxane (dried over Na). NaH (2.2 g, 50% in oil, washed in hexane, 0.046 moles) was added to the stirring solution and the slurry heated to 100° for 12 hours under N$_2$. After cooling to room temperature, the solid was allowed to settle. The upper solution was syringed into a dioxane solution of 2.5 g (0.03 moles) ethyl bromoacetate under N$_2$ and stirred for one hour.

The solution was filtered. The filtrate was diluted with ether and extracted with 1 N HCl. The HCl extract was made alkaline with 10% Na$_2$CO$_3$ and extracted three times with ether. The ether extracts were dried over MgSO$_4$. The solvent was removed on Rotovap, giving 3.2 g of crude oil. This oil was hydrolyzed without further purification. The ester can be purified by preparative tlc on silica using 75-25, ether—CHCl$_3$, saturated with NH$_3$ gas. Rf=0.6. The ester can be distilled, with some decomposition, at 120° at 0.001 mm Hg, giving a clear oil.

III. Preparation of N-Carboxylmethyl 4-Diisopropylamino-2-Phenyl-2-(2'-Pyridyl) Butyramide.

The 3.2 g of crude ester of Ex. II was dissolved in 5 ml MeOH and 0.350 g NaOH in 10 ml water was added and the mixture stirred for two hours. The solution was diluted with 20 ml H$_2$O and extracted with ether twice. The aqueous layer was acidified to pH1 with 10% HCl and the solution lyophilized. The resulting solid was stirred with 5% MeOH—CHCl$_3$ and filtered. The solvents were taken off to give a white foam; tlc: 75-25 ether—CHCl$_3$ sat. with NH$_3$; Rf=0.3.

The foam was further purified by preparative tlc (silica) using 1-9-30, H$_2$O: MeOH: CH$_2$Cl$_2$; Rf=0.3. The acid was eluted from silica with MeOH. The MeOH was taken off on rotovap and the foam redissolved in CH$_2$Cl$_2$, filtered and the solvent removed to give a white powder. IR of the solid (KBr) shows carboxylate anion, it is likely Na$^+$ ions were eluted from silica. Analysis of sample showed Na$^+$ present.

IV. Conjugation of Disopyramide Hapten to BSA, BGG

The acid of Ex. III (150 mg, 0.35 mmoles) was combined with 115 mg (0.56 mmoles) of DCC and 65 mg (0.56 mmoles) NHS in 2 ml dry CH$_2$Cl$_2$ and 5 ml dry THF. After 24 hours the precipitated urea was filtered and the filtrate evaporated. The solid residue was washed with hexane, redissolved in THF-CH$_2$Cl$_2$, treated with more DCC (230 mg) and 130 mg NHS and stirred overnight. The solution was filtered, evaporated, and the solid washed to remove excess DCC. The solid was triturated in 2.0 ml THF and 0.5 ml CH$_2$Cl$_2$ and more of the urea was filtered off. BSA (500 mg, Miles) was dissolved in pH8.2 phosphate buffer and cooled to 0°-5°. The NHS ester solution was added dropwise to the stirring solution, maintaining the pH at 8.2 with 10% Na$_2$CO$_3$. The pH was kept at 8.2-8.4 for one hour at 0°-5° then kept stirring in the cold room overnight.

The volume of protein solution was reduced to 14 ml with a collodion bag. The solution was divided into two fractions which were chromatographed on G-50 Sephadex (2.5×20 cm) with pH8 phosphate buffer. All protein fractions were combined and dialyzed three times with 4 l pH9-9.5 NH$_4$OH, then lyophilized to yield 400 mg.

The UV of the hapten in buffer was measured, giving λmax 260 with little absorption at 280. Therefore, hapten number was determined as 16. Conjugation to BGG was done in the same manner, giving 425 mg conjugate with disopyramide analog.

The N-hydroxysuccinimide ester was also prepared with DMF using EDCI. The acid (19.6 mg) and 5.4 mg of NHS were stirred in a dry flask with 500 µl of dry DMF (3a sieves). EDCI (10 mg) was added and the solution stirred overnight. Ratio of hapten:NHS:EDCI=1:1.04:1.15. A 5 µl aliquot was added to excess benzylamine. After diluting with CHCl$_3$ and pumping off solvent under vacuum, tlc showed little acid remaining.

V. Conjugation of Disopyramide Hapten to G6PDH

Into a reaction flask was introduced 19.6 mg of the acid of Ex. III, 5.4 mg of NHS, 10 mg of EDAC and 500 µl DMF and the mixture stirred overnight at room temperature.

A ~4 mg/ml G6PDH solution in 55 mM tris is diluted to 3 mls of enzyme solution: 1 ml of 1 M tris, pH8.3, followed by the addition of 80 mg G6PNa$_2$, 80 mg of NADH and 1.2 ml carbitol. While stirring the enzyme solution at 4°, the above NHS ester solution in 2 µl increments was added over a period of ~1.5 hours, monitoring the enzyme rate for deactivation and inhibitability by antidisopyramide. A total of 226 µl of the above solution was added to provide a mole ratio of disopyramide charged to enzyme of 185:1. Desalting of the product was achieved by passage over a Sephadex G-50 column equilibrated with 0.055 mM tris buffer. A maximum rate of ΔOD=660 in accordance with the protocol described hereinafter was achieved with 5 µl/ml dilution. With 50 µl of antidisopyramide added to the enzyme diluted solution ~80% inhibition was observed.

The antigens prepared above were injected into sheep and a number of bleeds taken. Injections were either at 0.5 mg or 1 mg levels. The bleeds were then tested for titer and employed in an immunoassay as described in U.S. Pat. No. 3,817,837.

The assay employed the following reagents.

TABLE I

Buffer: 0.055 M tris-HCl, pH8.1 (RT), 0.05% NaN$_3$, 0.005% Thimerosal

Assay Buffer: Buffer, 0.5% NaCl, 0.01% (V/V) Triton X-100, pH8.1 (RT)

Reagent A: Buffer, 1.0% RSA, G-6-P(Na$_2$), NAD, pH5 (RT), antidisopyramide optimized for assay Reagent B: Buffer, 0.9% NaCl, 1% RSA, pH8.1 (RT), sufficient enzyme conjugate to give a ΔOD in the range of 350-500

Calibrators: Levels 0, 0.5, 1, 2, 4, 8 µg/ml disopyramide

Protocol: 50 µl of the sample is drawn up into a diluter and dispensed with 250 µl of the assay buffer into a 1 ml Croan cup. A 50 µl aliquot of the diluted sample is drawn up and dispensed with a 250 µl portion of assay buffer into a second Croan cup. Into the second Croan cup is introduced 50 µl of the antibody reagent with 250 µl of the assay buffer, followed by the addition of 50 µl of the enzyme reagent and 250 µl of the assay buffer. Immediately after the enzyme addition, the entire sample is aspirated into the flow cell. After 15 sec a first reading is taken, followed by a second reading after a thirty second interval. The results are reported as the difference in absorbance×2.667.

Cross-reactivity was checked against methadone, alpha-acetylmethadone, propoxyphene and the monodealkylated metabolite. The indicated metabolite is considered to be the metabolite in greatest amount. Cross-reactivity for methadone and long acting methadone, with one exception required 50 or greater µg/ml of methadone to obtain the same signal obtained at 3 µg/ml of disopyramide. Propoxyphene showed no cross-reactivity and the metabolite required greater than 10 µg/ml for a result equivalent to 3 µg/ml of disopyramide.

When samples were analyzed against results obtained with gas-liquid chromatography the correlation observed was reasonably good (correlation coefficient, 0.85) in view of the uncertainties involved with the reference methods. It was therefore concluded that the antibody and enzyme conjugate were capable of providing a sensitive, accurate assay for disopyramide, without interference from other structurally similar compounds or materials normally encountered in serum.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

(A—CONHR(CO)$_m$)$_n$Z wherein:

A is of the formula:

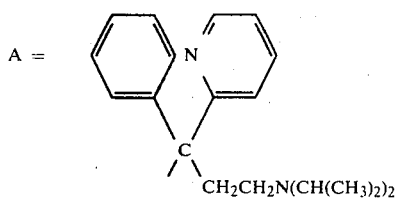

R is a saturated aliphatic linking group of from one to six carbon atoms;

Z is hydrogen, hydroxyl, alkoxyl, a group forming an activated ester capable of amide formation in an aqueous medium, or a polypeptide which is antigenic or an enzyme;

m is zero or one when Z is a poly(amino acid) and is otherwise one; and n is one when Z is other than a poly(amino acid) and is otherwise one to the molecular weight of Z divided by 500.

2. A compound according to claim 1, wherein R is polymethylene of from one to three carbon atoms.

3. A compound according to claim 2, wherein R is methylene.

4. A compound of the formula:

ACONHR$^1$COZ$^1$ wherein:

A is of the formula:

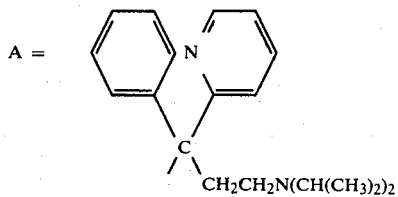

R$^1$ is a saturated aliphatic linking group of from one to three carbon atoms;

Z$^1$ is hydrogen, hydroxyl, alkoxy of from one to six carbon atoms, or a group forming an activated ester capable of amide formation in an aqueous medium.

5. A compound according to claim 4, wherein R$^1$ is methylene.

6. A compound of the formula:

(ACONHR$^2$(CO)$_{m2}$)$_{n2}$Z$^2$ wherein:

A is of the formula:

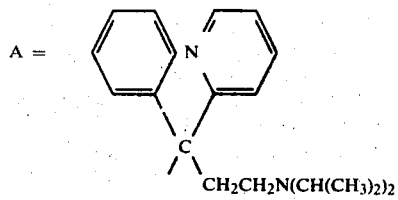

R$^2$ is a saturated aliphatic linking group of from one to three carbon atoms;

Z$^2$ is a poly(amino acid), which is antigenic or an enzyme;

m$^2$ is zero or one;

n$^2$ is at least one and not greater than the molecular weight of Z$^2$ divided by 1,000.

7. A compound according to claim 6, wherein R$^2$ is methylene.

8. A compound according to claims 6 and 7 wherein m$^2$ is one, n$^2$ is in the range of 2 to 500, and Z$^2$ is an antigen.

9. A compound according to claim 8 wherein R$^2$ is methylene and Z$^2$ is an albumin.

10. A compound according to claims 6 or 7 wherein m$^2$ is one, n$^2$ is in the range of 2 to 20 and Z$^2$ is an enzyme.

11. A compound according to claim 10, wherein Z$^2$ is glucose-6-phosphate dehydrogenase.

12. Antibodies prepared in response to a compound according to claim 6 wherein m$^2$ is one, n$^2$ is in the range of 2 to 500, and z$^2$ is an antigen, capable of binding to disopyramide, and said compound.

* * * * *